United States Patent
Zhuang et al.

(10) Patent No.: US 6,864,373 B2
(45) Date of Patent: Mar. 8, 2005

(54) STABLE AMORPHOUS CELECOXIB COMPOSITE AND PROCESS THEREFOR

(75) Inventors: Hong Zhuang, Portage, MI (US); Ping Gao, Portage, MI (US)

(73) Assignee: Pharmacia Corporation, St. Louis, MO (US)

( * ) Notice: Subject to any disclaimer, the term of this patent is extended or adjusted under 35 U.S.C. 154(b) by 84 days.

(21) Appl. No.: 10/431,853

(22) Filed: May 8, 2003

(65) Prior Publication Data

US 2004/0030151 A1 Feb. 12, 2004

Related U.S. Application Data

(60) Provisional application No. 60/379,968, filed on May 13, 2002.

(51) Int. Cl.[7] ............................................. C07D 231/22
(52) U.S. Cl. ................................................... 548/371.1
(58) Field of Search ....................................... 548/371.1

(56) References Cited

U.S. PATENT DOCUMENTS 5,466,823 A    11/1995  Talley et al. ............. 548/377.1
5,892,053 A    4/1999   Zhi et al. ................. 548/377.1
6,395,300 B1 *  5/2002   Straub et al. ................ 424/489

FOREIGN PATENT DOCUMENTS

WO   WO 00/32189   6/2000   ......... A61K/31/415
WO   WO 00/42021   7/2000   ......... C07D/231/12

OTHER PUBLICATIONS

Lieberman et al., (1989), Pharmaceutical Dosage Forms: Tablets, vol. 1, pp. 34–36.
The Merck Index, 12th Edition, Therapeutic Category and Biological Activity Index, ed. S. Budavari (1996), pp. Ther–2 to Ther–3 and Ther–12.

* cited by examiner

Primary Examiner—Johann Richter
Assistant Examiner—Ebenezer Sackey
(74) Attorney, Agent, or Firm—Patricia K. Fitzsimmons (57) ABSTRACT

A process is provided for preparing a celecoxib-crystallization inhibitor composite wherein at least a detectable amount of celecoxib is in amorphous form. Also provided are compositions prepared according to such a process. Also provided is a method of treating a medical condition or disorder in a subject where treatment with a cyclooxygenase-2 inhibitor is indicated, comprising administering, for example orally, a composition of the invention in a therapeutically effective amount.

44 Claims, 3 Drawing Sheets

STABLE AMORPHOUS CELECOXIB COMPOSITE AND PROCESS THEREFOR

The application claims priority of U.S. provisional Application Ser. No. 60/379,968 filed on May 13, 2002.

FIELD OF THE INVENTION

The present invention relates to the selective cyclooxygenase-2 inhibitory drug celecoxib and in particular to a process for preparing a stable composite comprising amorphous celecoxib, and to pharmaceutical compositions comprising such a composite. The invention further relates to methods of treatment of cyclooxygenase-2 mediated disorders comprising administering such amorphous composites or compositions thereof to a subject, and to use of such solid-state forms in the manufacture of medicaments.

BACKGROUND OF THE INVENTION

Celecoxib, also known as 4-[5-(4-methylphenyl)-3-(trifluoromethyl)-1H-pyrazol-1-yl]benzenesulfonamide (I), the active ingredient of Celebrex® marketed by Pharmacia Corp., has a therapeutically and prophylactically useful selective cyclooxygenase-2 inhibitory effect, and has utility in treatment and prevention of specific cyclooxygenase-2 mediated disorders and of such disorders in general. Celecoxib has the structure:

(I)

Processes for preparing celecoxib are set forth in U.S. Pat. No. 5,466,823 to Talley et al. and in U.S. Pat. No. 5,892,053 to Zhi & Newaz, both incorporated herein by reference. Co-assigned International Patent Publication No. WO 00/32189, incorporated herein by reference, discloses that celecoxib has a crystal morphology which tends to form long, cohesive needles. Co-assigned International Patent Publication No. WO 00/42021, incorporated herein by reference, discloses a solvated crystalline form of celecoxib and a method for desolvation of that crystalline form.

A need for new forms of celecoxib, in particular forms suitable for preparing rapid-onset compositions, exists. Rapid-onset drug-delivery systems can provide significant benefits over conventional dosage forms. Generally, rapid-onset preparations provide a short period to therapeutic or prophylactic response compared to conventional immediate-release or sustained-release dosage forms. For example, in treatment of acute pain, a rapid-onset dosage form of celecoxib would be useful to provide fast pain relief.

However, celecoxib presents certain challenges for formulation as a rapid-onset dosage form, particularly as a rapid-onset oral dosage form. For example, celecoxib has very low solubility in aqueous media (about 2 to about 5 μg/ml) and therefore is not readily dissolved and dispersed for rapid absorption in the gastrointestinal tract when administered orally, for example in tablet or capsule form. In addition, celecoxib has a relatively high dose requirement further increasing difficulties of providing a sufficient therapeutically effective dose for rapid absorption.

Celecoxib crystals also present formulation difficulties as a result of unique physical and chemical characteristics or mechanical properties such as electrostatic and cohesive properties, low bulk density, low compressibility and poor flow properties. Due at least in part to these properties, celecoxib crystals tend to segregate and agglomerate together during mixing, resulting in a non-uniformly blended composition containing undesirably large, insoluble aggregates of celecoxib. For these and other reasons, therefore, it is difficult to prepare an orally deliverable, rapid-onset composition containing celecoxib that has the desired blend uniformity.

The bioavailability of an orally administered drug, as measured by its entry into systemic circulation in the bloodstream, depends on at least two fundamental processes: drug dissolution in gastrointestinal fluids (in vivo drug release) and subsequent absorption of the dissolved drug. Several factors influence dissolution of a drug from its carrier, including surface area of the drug presented to the dissolution solvent medium, solubility of the drug substance in the solvent medium, and driving forces of the saturation concentration of dissolved materials in the solvent medium.

When the process of in vivo drug release is slower than the process of absorption, absorption is said to be dissolution rate-limited. Since dissolution precedes absorption in the overall process, any change in the drug release or dissolution process will subsequently influence drug absorption. See for example Lieberman et al. (1989), Pharmaceutical Dosage Forms: Tablets, Vol. 1, pp. 34–36. Marcel Dekker, New York. It is clear, therefore, that dissolution time determined for a composition is one of the important fundamental characteristics for consideration when evaluating compositions intended for fast-onset delivery, particularly where drug absorption is dissolution rate-limited.

Crystalline solids, due to their highly organized, lattice-like structures, typically require a significant amount of energy for dissolution. The energy required for a drug molecule to escape from a crystal, for example, is greater than is required for the same drug molecule to escape from a non-crystalline, amorphous form. Importantly, however, crystalline drug forms which have been transformed into amorphous forms tend to revert to a steady state of low energy, namely the crystalline form, over time and thus may not have an adequate shelf life.

As indicated hereinbelow, treatment with celecoxib is indicated in a very wide array of cyclooxygenase-2 mediated conditions and disorders. Therefore, if an amorphous form of celecoxib could be prepared, and in particular if a storage-stable composition comprising such an amorphous form of celecoxib could be developed exhibiting enhanced bioavailability, for example through rapid dissolution of the drug, a significant advance would be realized in treatment of cyclooxygenase-2 mediated conditions and disorders, particularly in treatment of acute disorders where early relief from pain or other symptoms is desired.

SUMMARY OF THE INVENTION

Celecoxib provides a more rapid onset of therapeutic effect if, upon oral administration of a composition comprising celecoxib, pharmacokinetic properties are exhibited leading to a greater maximum blood serum concentration ($C_{max}$) and/or a shorter time following the administration to reach that maximum ($T_{max}$). It is contemplated that a greater $C_{max}$ and/or a shorter $T_{max}$ can result from faster dissolution of celecoxib when provided in amorphous form than in crystalline form.

Accordingly, the present invention provides a process for preparing a celecoxib-crystallization inhibitor composite wherein at least a detectable amount of the celecoxib is in amorphous form, the process comprising the steps of: (a) dissolving celecoxib in at least one pharmaceutically acceptable solvent for the celecoxib to form a first solution; (b) dissolving at least one crystallization inhibitor (selected according to Test I described hereinbelow) in at least one pharmaceutically acceptable solvent for the crystallization inhibitor to form a second solution; (c) adding the first solution to the second solution at a rate of not more than about 20%, by volume, of the first solution per second to form a mixture; (d) equilibrating the mixture for a period of time effective to result in precipitation of a celecoxib-crystallization inhibitor composite from the mixture; and (e) separating the celecoxib-crystallization inhibitor composite from the mixture.

The term "adding the first solution to the second solution" includes transferring a volume of first solution from a first vessel into a second vessel which contains the second solution, and/or simultaneously or substantially simultaneously transferring an amount of the first solution from a first vessel and an amount of second solution from a second vessel into a third vessel.

The term "equilibrating" herein refers to providing conditions (e.g. temperature, stirring, ratio of mixture volume to container volume, etc.) under which a celecoxib-crystallization inhibitor composite will gradually precipitate over time. Preferably, the equilibrating step comprises moderate agitation of the mixture at room temperature for a period of at least about 1 hour. Such agitation can be performed in any suitable manner, for example by shaking, rolling or tumbling the mixture or stirring the mixture with a paddle or stir bar.

At least a detectable amount of celecoxib present in a celecoxib-crystallization inhibitor composite prepared according to a process of the invention is in amorphous form, and the celecoxib is in intimate association with the at least one crystallization inhibitor. An "intimate association" in the present context includes, for example, celecoxib embedded or incorporated in the crystallization inhibitor, celecoxib forming a coating on particles of the crystallization inhibitor or vice versa, and/or a substantially homogeneous dispersion of celecoxib throughout the crystallization inhibitor. The term "substantially homogeneous" herein with reference to a composite or pharmaceutical composition that comprises multiple components means that the components are sufficiently mixed such that individual components are not present as discrete layers and do not form concentration gradients within the composition.

The present invention also provides a pharmaceutical composition comprising a celecoxib-crystallization inhibitor composite, for example a celecoxib-polymer composite prepared by a process of the invention. Such a composition can comprise dose units that can be in the form of discrete solid articles such as tablets, caplets, pills, hard or soft capsules, lozenges, sachets or pastilles; alternatively the composition can be in the form of a substantially homogeneous flowable mass, such as a particulate or granular solid or a liquid suspension, for example an imbibable dispersion, from which single dose units are measurably removable.

Also provided is a method of treating a medical condition or disorder in a subject where treatment with a cyclooxygenase-2 inhibitor is indicated, comprising administering, for example orally, a composition of the invention in a therapeutically effective amount. Such a method is particularly useful where the medical condition or disorder is accompanied by acute pain.

A celecoxib-crystallization inhibitor composite prepared according to a process of the invention is particularly advantageous due to its exhibition of good physical stability (i.e. the celecoxib tends to remain stabilized in amorphous form over time). Without being bound by theory, it is believed that the presence of stable, amorphous celecoxib particles facilitates faster drug dissolution and more rapid onset of therapeutic effect. Other features of this invention will be in part apparent and in part pointed out hereinafter.

DETAILED DESCRIPTION OF THE INVENTION

Celecoxib-crystallization Inhibitor Composite

The invention provides a process for preparing a celecoxib-crystallization inhibitor composite in which at least a detectable amount of the celecoxib present therein is in amorphous form. The term "amorphous" as used herein refers to solid-state particles lacking a regular crystalline structure. Without being bound by theory, it is believed that amorphous celecoxib particles require less energy for dissolution than crystalline celecoxib particles of similar dimensions, and that this reduced dissolution energy requirement contributes, at least in part, to increased dissolution rate and/or decreased therapeutic onset time exhibited by amorphous celecoxib and compositions thereof.

At least a detectable amount of celecoxib in a celecoxib-crystallization inhibitor composite of the invention is in amorphous form. In one embodiment, about 10% to 100%, preferably about 25% to 100%, and still more preferably about 60% to 100%, by weight, of celecoxib present in the composite is in amorphous form. In a celecoxib-crystallization inhibitor composite of this embodiment, a fraction of the celecoxib can be present as microcrystalline or nanocrystalline celecoxib, though this fraction is preferably small, for example less than about 50%, more preferably less than about 25%, still more preferably less than about 10%, and even more preferably less than about 5%, by weight of the total celecoxib in the composite.

In another embodiment, the amount of amorphous celecoxib in a celecoxib-crystallization inhibitor composite prepared according to a process of the invention is sufficient to provide increased dissolution rate as measured in a standard in vitro dissolution assay and/or improved bioavailability (e.g., shorter time to reach a threshold therapeutic concentration in blood plasma, greater $C_{max}$ and/or shorter $T_{max}$) as measured in a standard in vivo pharmacokinetic study, compared with an otherwise similar celecoxib-polymer composite wherein all, or a substantial portion of, the celecoxib is crystalline.

A celecoxib-crystallization inhibitor composite prepared according to a process of the invention, depending on the particular crystallization inhibitor(s) used, preferably comprises about 10% to about 80%, preferably about 15% to about 75%, and more preferably about 25% to about 65%, by weight, of the crystallization inhibitor. Preferably, the weight ratio of celecoxib to crystallization inhibitor in a celecoxib-crystallization inhibitor composite prepared by a process of the invention is about 1:8 to about 8:1, more preferably about 1:5 to about 5:1, and still more preferably about 1:2 to about 2:1.

In another embodiment, a celecoxib-crystallization inhibitor composite prepared according to a process of the invention comprises an amount of crystallization inhibitor which is sufficient such that when the composite is maintained in an open dish at ambient temperature for a period of at least 7 days, transformation of amorphous celecoxib to crystalline celecoxib is no greater than about 50%, preferably no greater than about 25%, and more preferably no greater than about 10%, by weight of all celecoxib in the composite.

Crystallization Inhibitors

Crystallization inhibitors include any material which substantially reduces conversion of amorphous celecoxib to crystalline celecoxib, for example, polymers, carbohydrates, lipids, etc. The term "substantially reduces" with respect to a crystallization inhibitor reducing conversion of amorphous celecoxib to crystalline celecoxib includes completely inhibiting, preventing, slowing, delaying, decreasing or restricting crystallization of celecoxib to a measurable degree. In general, a suitable crystallization inhibitor can be selected according to Test I.

Test I.

A. Celecoxib is dissolved in ethanol at a concentration of 5 to 100 mg/ml with stirring to form a first solution;

B. A test material is selected and is dissolved in 100 ml of room temperature water (with stirring and optionally heat) to form a second solution; the concentration of test material in the water should be about 1% wt/wt;

C. The first solution is added to the second solution at a rate of about 0.02 ml per second (with stirring) to form a mixture in which the celecoxib concentration is about 200 µg/ml to about 1000 µg/ml;

D. The mixture is stirred at room temperature for a period of at least 48 hours;

E. After 48 hours of stirring, a sample of the mixture is drawn and concentration of celecoxib in solution is determined;

F. If the concentration of celecoxib in solution in the sample is not less than 10 µg/ml, the test material is deemed suitable for use as a crystallization inhibitor in a process of the invention; if the concentration of celecoxib in solution in the sample is less than 10 µg/ml, the test material is deemed to be unsuitable for use as a crystallization inhibitor in a process of the invention.

In a particularly preferred embodiment, a crystallization inhibitor placed in Test I is deemed suitable if the concentration of celecoxib in solution in the sample drawn in step E is greater than 20 µg/ml after 48 hours of stirring.

HPMC (hydroxy-propylmethyl cellulose) and methylcellulose are preferred polymers. HPMCs are particularly preferred polymers for use as crystallization inhibitors in processes and compositions of the invention. HPMCs vary in the chain length of their cellulosic backbone and consequently in their viscosity as measured for example at a 2% by weight concentration in water. HPMC used in processes and celecoxib-polymer composites of the invention should have a viscosity, 2% in water, of about 5 to about 100,000 cP, preferably about 5 to about 15,000 cP. Molecular weight of HPMC used in celecoxib-polymer composites of the invention is preferably greater than about 10,000 but preferably not greater than about 1,500,000, more preferably not greater than about 1,000,000, still more preferably not greater than about 500,000, and even more preferably not greater than about 150,000. HPMCs also vary in the relative degree of substitution of available hydroxyl groups on the cellulosic backbone by methoxy and hydroxypropoxy groups. With increasing hydroxypropoxy substitution, the resulting HPMC becomes more hydrophilic in nature. It is preferred in celecoxib-HPMC composites of the present invention to use HPMC having about 15% to about 35%, preferably about 19% to about 32%, and more preferably about 22% to about 30%, methoxy substitution, and having about 3% to about 15%, preferably about 4% to about 12%, and more preferably about 7% to about 12%, hydroxypropoxy substitution. HPMCs which can be used in the present invention are illustratively available under the brand names Methocel™ of Dow Chemical Co. and Metolose™ of Shin-Etsu Chemical Co. Examples of particularly suitable HPMCs having low and medium viscosities include Methocel™ E5 which has a viscosity, 2% in water, of about 5 cP, and Methocel™ E4M and Methocel™ K4M, both of which have a viscosity, 2% in water, of about 4000 cP. Examples of HPMCs having higher viscosity include Methocel™ E10M, Methocel™ K15M and Methocel™ K100M, which have viscosities, 2% in water, of 10,000 cP, 15,000 cP and 100,000 cP respectively.

Process for Preparing a Celecoxib-crystallization Inhibitor Composite

In a presently preferred embodiment of the invention there is provided a process for preparing a celecoxib-crystallization inhibitor composite comprising celecoxib, at least a detectable portion of which is in amorphous form, and a crystallization inhibitor in intimate association with the celecoxib. The process comprises the steps of (a) dissolving celecoxib in at least one pharmaceutically acceptable solvent for the celecoxib to form a first solution; (b) dissolving at least one crystallization inhibitor in at least one pharmaceutically acceptable solvent for the crystallization inhibitor to form a second solution (preferably with heat); (c) adding the first solution to the second solution at a rate of not more than about 20%, by volume, of the first solution per second to form a liquid mixture; (d) equilibrating the mixture for a period of time effective to result in precipitation of a celecoxib-crystallization inhibitor composite from the mixture; and (e) separating the precipitated celecoxib-crystallization inhibitor composite from the mixture. Steps (a) and (b) can be performed in any order or substantially simultaneously.

The term "pharmaceutically acceptable solvent for the celecoxib" means that the solvent should be capable of dissolving relevant quantities of celecoxib, preferably with moderate stirring at room temperature, and should be suitable for administration to a human subject. The term "pharmaceutically acceptable solvent for the at least one crystallization inhibitor" means that the solvent should be capable of dissolving relevant quantities of the crystallization inhibitor(s), preferably with moderate stirring, and should be suitable for administration to a human subject. A technician will, through routine experimentation, readily identify pharmaceutically acceptable solvent(s) for the celecoxib and for the crystallization inhibitor(s). In some cases, a solvent may be acceptable for both celecoxib and the crystallization inhibitor(s) while in other cases, more than one solvent will be used.

Non-limiting examples of suitable pharmaceutically acceptable solvents for celecoxib include water-alcohol mixtures, methanol, ethanol, n-butanol, isopropanol, higher alcohols, propylene glycol, dimethylamide, diethyl glycol monoethyl ether (DGME), polyethylene glycols (PEGs), etc. Non-limiting examples of suitable pharmaceutically acceptable solvents for the crystallization inhibitor include water, water/alcohol mixtures, alcohols (e.g. ethanol), propylene glycol, ethyl caprylate, propylene glycol laurate, PEGs, tetraethylene glycol dimethyl ether, triethylene glycol monoethyl ether, etc.

In a process of the invention, the celecoxib concentration in the first solution is preferably not less than about 1 mg/ml, for example about 2.5 mg/ml to about 400 mg/ml, and preferably about 5 mg/ml to about 200 mg/ml. The concentration of crystallization inhibitor in the second solution is preferably not less than about 0.1% wt/wt, for example about 0.1% to about 20%, wt/wt, and preferably about 1% wt/wt to about 20% wt/wt. One of ordinary skill in the art will readily select a suitable crystallization inhibitor concentration within the ranges provided herein depending on, inter alia, the particular crystallization inhibitor(s) and solvent(s) being used, the rate of combination of the first and second solutions, and the celecoxib concentration in the first solution.

Regardless of the concentration of celecoxib in the first solution or the concentration of crystallization inhibitor(s) in the second solution, the initial (i.e. prior to any substantial amount of precipitation) concentration of celecoxib in solution in the mixture formed from step (c) is preferably not less than about 25 µg/ml, for example about 30 µg/ml to about 5000 µg/ml, preferably about 40 µg/ml to about 2500 µg/ml, and more preferably about 50 µg/ml to about 1000 µg/ml. Regardless of the concentration of celecoxib in the first solution or the concentration of the crystallization inhibitor(s) in the second solution, the initial concentration of crystallization inhibitor in the mixture resulting from step (c) (prior to any substantial amount of precipitation) is preferably not less than about 0.01% wt/wt, for example about 0.1% wt/wt to about 15% wt/wt and preferably about 0.1% wt/wt to about 5% wt/wt.

Preferably, in step (c), the first solution is added to the second solution at a rate of about 0.1% to about 10%, more preferably about 0.1% to about 7.5%, and still more preferably about 0.1% to about 5%, by volume, of the first solution being combined with the second solution, per second. Importantly, one of ordinary skill in the art will be able to readily optimize rate of combination of the first and second solutions within the ranges provided herein such that the process will be applicable to any desired scale of production. Step (c) is preferably performed at a temperature of about 18 to about 30° C., and more preferably at about 20 to about 25° C. In a preferred embodiment, the mixture resulting from step (c) is continuously agitated as it is formed.

Equilibrating step (d) comprises agitation of the mixture prepared in step (c), preferably at a temperature of about 18 to about 30° C., and more preferably at about 20 to about 25° C. The term "period of time effective to result in precipitation of a celecoxib-crystallization inhibitor composite from the mixture", with respect to length of the equilibrating step, generally means a length of time sufficient for a celecoxib-crystallization inhibitor composite to precipitate from the mixture in the form of precipitate which can be separated, using standard filtration or centrifugation techniques, from the mixture. In general, the period of time effective to result in precipitation of a celecoxib-crystallization inhibitor composite from the mixture will be at least about 5 minutes, preferably about 1 to about 60 days, more preferably about 1 to about 30 days, and still more preferably about 1 to about 21 days.

Any suitable separation means can be employed to separate precipitate from the mixture according to step (e). Illustrative, the precipitated celecoxib-crystalization inhibitor composite can be separated from the mixture by filtration, centrifugation, evaporation, freeze drying, conventional heating (e.g. in an oven), spray drying, etc. Filtration is a preferred method of separation.

A celecoxib-crystallization inhibitor composite prepared according to a process of the invention can be administered orally, rectally or parenterally without further formulation, or in simple suspension in water or another pharmaceutically acceptable liquid. Alternatively, the composite can be directly filled into capsules for oral administration. Preferably, however, the composite or powder thereof is subjected to further processing, typically with one or more additional excipients, to prepare a pharmaceutical composition, for example an oral dosage form, as described hereinbelow.

Pharmaceutical Compositions

A celecoxib-crystallization inhibitor composite as provided herein can be further formulated together with one or more pharmaceutically acceptable excipients to produce a pharmaceutical composition. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients include, by way of illustration and not limitation, diluents, disintegrants, binding agents, adhesives, wetting agents, lubricants, glidants, crystallization inhibitors, surface modifying agents, substances added to mask or counteract a disagreeable taste or odor, flavors, dyes, fragrances, and substances added to improve appearance of the composition.

Excipients employed in compositions of the invention can be solids, semi-solids, liquids or combinations thereof. Compositions of the invention containing excipients can be prepared by any known technique of pharmacy that comprises admixing an excipient with a drug or therapeutic agent. A composition of the invention contains a desired amount of celecoxib per dose unit and, if intended for oral administration, can be in the form, for example, of a tablet, a caplet, a pill, a hard or soft capsule, a lozenge, a cachet, a dispensable powder, granules, a suspension, an elixir, a liquid, or any other form reasonably adapted for such administration. If intended for parenteral administration, it can be in the form, for example, of a suspension. If intended for rectal administration, it can be in the form, for example, of a suppository. Presently preferred are oral dosage forms that are discrete dose units each containing a predetermined amount of the drug, such as tablets or capsules.

Non-limiting examples follow of excipients that can be used to prepare pharmaceutical compositions of the invention.

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents, if present, constitute in total about 5% to about 99%, preferably about 10% to about 85%, and more preferably about 20% to about 80%, of the total weight of the composition. The diluent or diluents selected preferably exhibit suitable flow properties and, where tablets are desired, compressibility.

Lactose and microcrystalline cellulose, either individually or in combination, are preferred diluents. Both diluents are chemically compatible with celecoxib. The use of extragranular microcrystalline cellulose (that is, microcrystalline cellulose added to a wet granulated composition after a drying step) can be used to improve hardness (for tablets) and/or disintegration time. Lactose, especially lactose monohydrate, is particularly preferred. Lactose typically provides compositions having suitable release rates of celecoxib, stability, pre-compression flowability, and/or drying properties at a relatively low diluent cost. It provides a high density substrate that aids densification during granulation (where wet granulation is employed) and therefore improves blend flow properties.

Compositions of the invention optionally comprise one or more pharmaceutically acceptable disintegrants as excipients, particularly for tablet formulations. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated compositions of the present invention.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, preferably about 0.75% to about 15%, and more preferably about 1% to about 10%, of the total weight of the composition.

Compositions of the invention optionally comprise one or more pharmaceutically acceptable wetting agents as excipients. Such wetting agents are preferably selected to maintain the celecoxib in close association with water, a condition that is believed to improve bioavailability of the composition.

Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the composition.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the composition.

Compositions of the invention optionally comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium, calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the composition.

Magnesium stearate is a preferred lubricant used, for example, to reduce friction between the equipment and granulated mixture during compression of tablet formulations.

Suitable anti-adherents include talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the composition.

Glidants can be used to promote powder flow of a solid formulation. Suitable glidants include colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in compositions of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of compositions of the invention. When present in compositions of the invention to promote dosage form disintegration, one or more effervescent agents are preferably present in a total amount of about 30% to about 75%, and preferably about 45% to about 70%, for example about 60%, by weight of, the composition.

According to a particularly preferred embodiment of the invention, an effervescent agent, present in a solid dosage form in an amount less than that effective to promote disintegration of the dosage form, provides improved dispersion of the celecoxib in an aqueous medium. Without being bound by theory, it is believed that the effervescent agent is effective to accelerate dispersion of celecoxib from the dosage form in the gastrointestinal tract, thereby further enhancing absorption and rapid onset of therapeutic effect. When present in a pharmaceutical composition of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the composition.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base.

Non-limiting examples of suitable acids as components of effervescent agents useful in the invention include citric acid, tartaric acid, malic acid, fumaric acid, adipic acid, succinic acid, acid anhydrides of such acids, acid salts of such acids, and mixtures thereof. Citric acid is a preferred acid.

In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Solid dosage forms of the invention can be prepared by any suitable process, not limited to processes described herein.

An illustrative process comprises (a) a step of blending a celecoxib-crystallization inhibitor composite of the invention with one or more excipients to form a blend, and (b) a step of tableting or encapsulating the blend to form tablets or capsules respectively.

In a preferred process, solid dosage forms are prepared by a process comprising (a) a step of blending a celecoxib-crystallization inhibitor composite of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a wet granulation step followed by a step of drying the resulting granulate prior to tableting or encapsulating. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in drug content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein the celecoxib-crystallization inhibitor composite is suspended with one or more excipients in one or more sprayable liquids, preferably a non-aqueous sprayable liquid, and then is rapidly spray dried over a current of warm air.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

Any tablet hardness convenient with respect to handling, manufacture, storage and ingestion can be employed. For example, for 100 mg celecoxib tablets, hardness is preferably at least about 4 kP, more preferably at least about 5 kP, and still more preferably at least about 6 kP. For 200 mg celecoxib tablets, hardness is preferably at least about 7 kP, more preferably at least about 9 kP, and still more preferably at least about 11 kP. The material to be tableted, however, should not be compressed to such a degree that there is subsequent difficulty in achieving hydration when exposed to gastric fluid.

Tablet friability preferably is less than about 1.0%, more preferably less than 0.8%, and still more preferably less than about 0.5% in a standard test.

Celecoxib Dosage

Celecoxib dosage forms of the invention preferably comprise celecoxib in a daily dosage amount of about 10 mg to about 1000 mg, more preferably about 25 mg to about 400 mg, and most preferably about 50 mg to about 200 mg.

Compositions of the invention comprise one or more orally deliverable dose units. Each dose unit comprises celecoxib in a therapeutically effective amount that is preferably about 10 mg to about 1000 mg. The term "dose unit" herein means a portion of a pharmaceutical composition that contains an amount of a therapeutic or prophylactic agent, in the present case celecoxib, suitable for a single oral administration to provide a therapeutic effect. Typically one dose unit, or a small plurality (up to about 4) of dose units, in a single administration provides a dose comprising a sufficient amount of the agent to result in the desired effect. Administration of such doses can be repeated as required, typically at a dosage frequency of 1 to about 4 times per day.

It will be understood that a therapeutically effective amount of celecoxib for a subject is dependent inter alia on the body weight of the subject. A "subject" herein to which a therapeutic agent or composition thereof can be administered includes a human patient of either sex and of any age, and also includes any nonhuman animal, particularly a warm-blooded animal, more particularly a domestic or companion animal, illustratively a cat, dog or horse. When the subject is a child or a small animal (e.g., a dog), for example, an amount of celecoxib relatively low in the preferred range of about 10 mg to about 1000 mg is likely to provide blood serum concentrations consistent with therapeutic effectiveness. Where the subject is an adult human or a large animal (e.g., a horse), achievement of such blood serum concentrations of celecoxib are likely to require dose units containing a relatively greater amount of celecoxib.

Typical dose units in a composition of the invention contain about 10, 20, 25, 37.5, 50, 75, 100, 125, 150, 175, 200, 250, 300, 350 or 400 mg of celecoxib. For an adult human, a therapeutically effective amount of celecoxib per dose unit in a composition of the present invention is typically about 50 mg to about 400 mg. Especially preferred amounts of celecoxib per dose unit are about 100 mg to about 200 mg, for example about 100 mg or about 200 mg.

A dose unit containing a particular amount of celecoxib can be selected to accommodate any desired frequency of administration used to achieve a desired daily dosage. The daily dosage and frequency of administration, and therefore the selection of appropriate dose unit, depends on a variety of factors, including the age, weight, sex and medical condition of the subject, and the nature and severity of the condition or disorder, and thus may vary widely.

The term "oral administration" herein includes any form of delivery of a therapeutic agent or a composition thereof to a subject wherein the agent or composition is placed in the mouth of the subject, whether or not the agent or composition is immediately swallowed. Thus "oral administration" includes buccal and sublingual as well as esophageal administration. Absorption of the agent can occur in any part or parts of the gastrointestinal tract including the mouth, esophagus, stomach, duodenum, ileum and colon. The term "orally deliverable" herein means suitable for oral administration.

Compositions of the invention are useful in treatment and prevention of a very wide range of disorders mediated by COX-2, including but not restricted to disorders characterized by inflammation, pain and/or fever. Such compositions are especially useful as anti-inflammatory agents, such as in treatment of arthritis, with the additional benefit of having significantly less harmful side effects than compositions of conventional nonsteroidal anti-inflammatory drugs (NSAIDs) that lack selectivity for COX-2 over COX-1. In particular, compositions of the invention have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs. Thus compositions of the invention are particularly useful as an alternative to conventional NSAIDs where such NSAIDs are contraindicated, for example in patients with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems; kidney disease; or in patients prior to surgery or patients taking anticoagulants.

Contemplated compositions are useful to treat a variety of arthritic disorders, including but not limited to rheumatoid arthritis, spondyloarthropathies, gouty arthritis, osteoarthritis, systemic lupus erythematosus and juvenile arthritis.

Such compositions are useful in treatment of asthma, bronchitis, menstrual cramps, preterm labor, tendinitis, bursitis, allergic neuritis, cytomegalovirus infectivity, apoptosis including HIV-induced apoptosis, lumbago, liver disease including hepatitis, skin-related conditions such as psoriasis, eczema, acne, burns, dermatitis and ultraviolet radiation damage including sunburn, and post-operative inflammation including that following ophthalmic surgery such as cataract surgery or refractive surgery.

Such compositions are useful to treat gastrointestinal conditions such as inflammatory bowel disease, Crohn's disease, gastritis, irritable bowel syndrome and ulcerative colitis.

Such compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

Such compositions are useful in treatment of ophthalmic diseases, such as retinitis, conjunctivitis, retinopathies, uveitis, ocular photophobia, and of acute injury to the eye tissue.

Such compositions are useful in treatment of pulmonary inflammation, such as that associated with viral infections and cystic fibrosis, and in bone resorption such as that associated with osteoporosis.

Such compositions are useful for treatment of certain central nervous system disorders, such as cortical dementias including Alzheimer's disease, neurodegeneration, and central nervous system damage resulting from stroke, ischemia and trauma. The term "treatment" in the present context includes partial or total inhibition of dementias, including Alzheimer's disease, vascular dementia, multi-infarct dementia, pre-senile dementia, alcoholic dementia and senile dementia.

Such compositions are useful in treatment of allergic rhinitis, respiratory distress syndrome, endotoxin shock syndrome and liver disease.

Such compositions are useful in treatment of pain, including but not limited to postoperative pain, dental pain, muscular pain, and pain resulting from cancer. For example, such compositions are useful for relief of pain, fever and inflammation in a variety of conditions including rheumatic fever, influenza and other viral infections including common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, bums, and trauma following surgical and dental procedures.

Such compositions are useful for treating and preventing inflammation-related cardiovascular disorders, including vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

Such compositions are useful in treatment of angio genesis-related disorders in a subject, for example to inhibit tumor angiogenesis. Such compositions are useful in treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

Such compositions are useful in prevention and treatment of benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreatic cancer, ovarian cancer, prostate cancer, cervical cancer, lung cancer, breast cancer and skin cancer. Such compositions can also be used to treat fibrosis that occurs with radiation therapy. Such compositions can be used to treat subjects having adenomatous polyps, including those with familial adenomatous polyposis (FAP). Additionally, such compositions can be used to prevent polyps from forming in patients at risk of FAP.

Such compositions inhibit prostanoid-induced smooth muscle contraction by inhibiting synthesis of contractile prostanoids and hence can be of use in treatment of dysmenorrhea, premature labor, asthma and eosinophil-related disorders. They also can be of use for decreasing bone loss particularly in postmenopausal women (i.e., treatment of osteoporosis), and for treatment of glaucoma.

Preferred uses for compositions of the invention are for treatment of rheumatoid arthritis and osteoarthritis, for pain management generally (particularly post-oral surgery pain, post-general surgery pain, post-orthopedic surgery pain, and acute flares of osteoarthritis), for treatment of Alzheimer's disease, and for colon cancer chemoprevention.

Besides being useful for human treatment, compositions of the invention are useful for veterinary treatment of companion animals, exotic animals, farm animals, and the like, particularly mammals. More particularly, compositions of the invention are useful for treatment of COX-2 mediated disorders in horses, dogs and cats.

The present invention is further directed to a therapeutic method of treating a condition or disorder where treatment with a COX-2 inhibitory drug is indicated, the method comprising oral administration of a composition of the invention to a subject in need thereof. The dosage regimen to prevent, give relief from, or ameliorate the condition or disorder preferably corresponds to once-a-day or twice-a-day treatment, but can be modified in accordance with a variety of factors. These include the type, age, weight, sex, diet and medical condition of the subject and the nature and severity of the disorder. Thus, the dosage regimen actually employed can vary widely and can therefore deviate from the preferred dosage regimens set forth above.

Initial treatment can begin with a dose regimen as indicated above. Treatment is generally continued as necessary over a period of several weeks to several months or years until the condition or disorder has been controlled or eliminated. Subjects undergoing treatment with a composition of the invention can be routinely monitored by any of the methods well known in the art to determine effectiveness of therapy. Continuous analysis of data from such monitoring permits modification of the treatment regimen during therapy so that optimally effective doses are administered at any point in time, and so that the duration of treatment can be determined. In this way, the treatment regimen and dosing schedule can be rationally modified over the course of therapy so that the lowest amount of the composition exhibiting satisfactory effectiveness is administered, and so that administration is continued only for so long as is necessary to successfully treat the condition or disorder.

The present compositions can be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise use of a composition of the invention with one or more compounds selected from aceclofenac, acemetacin, e-acetamidocaproic acid, acetamninophen, acetaminosalol, acetanilide, acetylsalicylic acid (aspirin), S-adenosylrnethiorine, alclofenac, alfentanil, allylprodine, alminoprofen, aloxiprin, alphaprodine, aluminum bis (acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolnetin guacil, anileridine, antipyrine, antipyrine salicylate, antrafenine, apazone, bendazac, benorylate, benoxaprofen, benzpiperylon, benzydamine, benzylmorphine, bermoprofen, bezitranude, α-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, ctofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic: acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lornoxican, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyfine, parsaimide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac (see *The Merck Index*, 12th Edition, Therapeutic Category and Biological Activity Index, ed. S. Budavari (1996), pp. Ther-2 to Ther-3 and Ther-12 (Analgesic (Dental), Analgesic (Narcotic), Analgesic (Non-narcotic), Anti-inflammatory (Nonsteroidal)).

Particularly preferred combination therapies comprise use of a composition of the invention with an opioid compound, more particularly where the opioid compound is codeine, meperidine, morphine or a derivative thereof.

A celecoxib composition of the invention can also be administered in combination with a second selective COX-2 inhibitory drug, for example valdecoxib, parecoxib, rofecoxib, etc.

The compound to be administered in combination with celecoxib can be formulated separately from the celecoxib or co-formulated with the celecoxib in a composition of the invention. Where celecoxib is co-formulated with a second drug, for example an opioid drug, the second drug can be formulated in immediate-release, rapid-onset, sustained-release or dual-release form.

EXAMPLES

The following examples illustrate aspects of the present invention but are not to be construed as limitations.

Example 1

Figure 1:
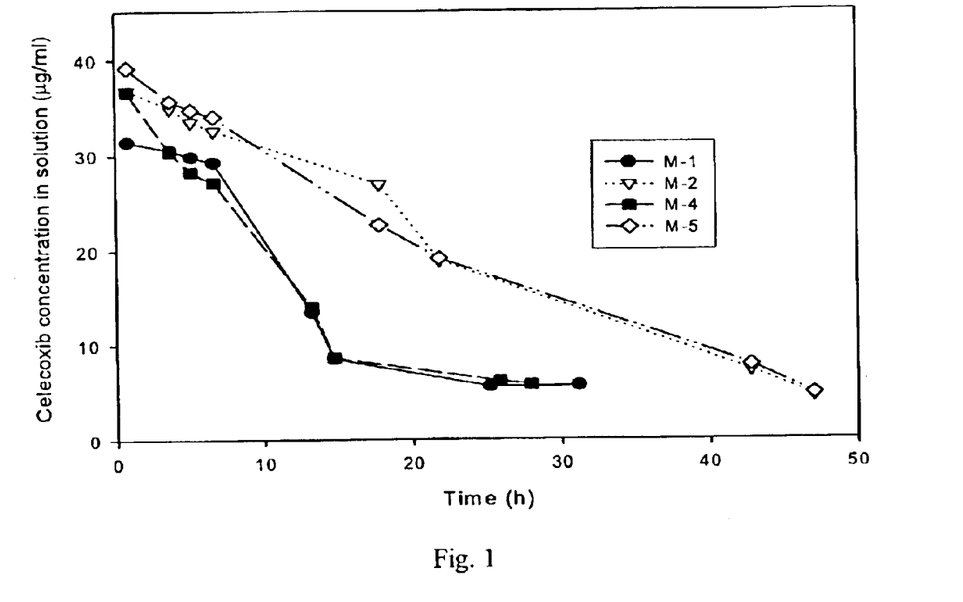
FIG. 1 shows concentration of celecoxib in solution in mixtures M-1, M-2, M-4 and M-5 at different times after preparation.

Six mixtures, M-1 to M-6, containing celecoxib and polyvinylpyrrolidone (PVP) were prepared having compositions shown in Table 1. The mixtures were prepared by dissolving between 5 and 100 mg celecoxib per ml of ethanol to form a first solution, dissolving PVP in water (with stirring at room temperature) to form a second solution having a PVP concentration of 0.2% to 2.5%, and transferring 1 ml of the first solution into the second solution at a rate of 0.02 ml of first solution per second to form a mixture. Each of the mixtures were agitated at room temperature using a stir bar maintained at 50 rpm for at least seven days. At various time points during stirring, aliquots of mixtures M-1, M-2, M-4, or M-5 were drawn and concentration of celecoxib in solution therein was measured. As shown in FIG. 1, mixture M-1 (which had a PVP concentration of 0.2%) maintained celecoxib in solution at a concentration greater than about 10 µg/ml for a period of not more than about 13 hours; by 30 hours, the celecoxib concentration in solution was less than 10 µg/ml. Mixture M-2 which had a PVP concentration of 1% maintained celecoxib in solution at a concentration greater than 10 µg/ml for a period of only about 21 to about 42 hours. Mixture M-4 which had a PVP concentration of 0.2% maintained celecoxib in solution at a concentration greater than 10 µg/ml for a period of not more than 14 hours. Mixture M-5 which had a PVP concentration of 1.0% maintained celecoxib in solution at a concentration greater than 10 µg/ml for a period of about 21 to about 42 hours.

TABLE 1

Composition of celecoxib/PVP mixtures M-1 to M-6

| Composition | M-1 | M-2 | M-3 | M-4 | M-5 | M-6 |
|---|---|---|---|---|---|---|
| Celecoxib (µg/ml) | 200 | 200 | 200 | 500 | 500 | 500 |
| Ethanol (% wt/wt) | 1 | 1 | 1 | 1 | 1 | 1 |
| PVP (% wt/wt) | 0.2 | 1.0 | 2.5 | 0.2 | 1.0 | 2.5 |
| Water (% wt/wt) | to 100 | to 100 | to 100 | to 100 | to 100 | to 100 |

Figure 2:
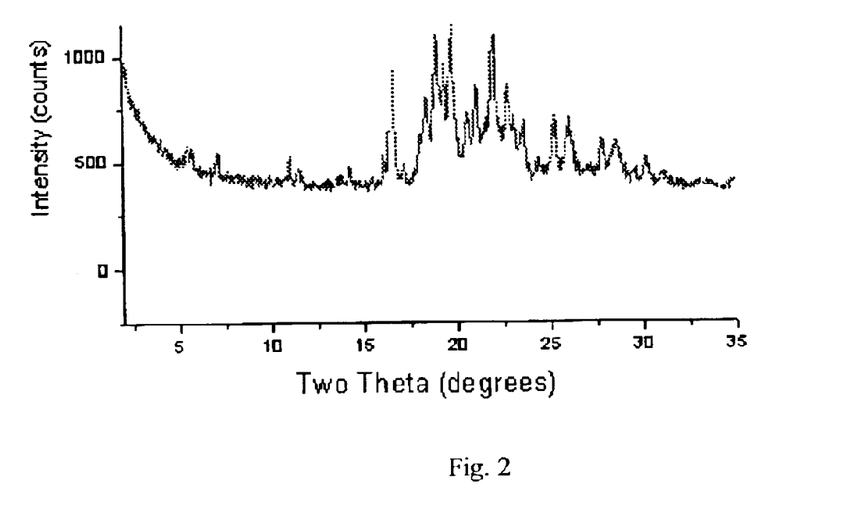
FIG. 2 shows an X-Ray diffraction profile of precipitate separated from mixture M-6 of Example 1.

A second batch of mixture M-6 was prepared and stirred for four days. After four days, precipitated solids were collected from mixture M-6 by filtration; the extracted precipitate was washed with water triplicate to form a paste solid. A portion of the paste solid was analyzed for the presence of crystalline material using X-Ray diffraction. As shown in FIG. 2, the precipitated solids were metastable crystalline form. In a third batch of M-6 mixture, precipitated solids were collected after seven days of stirring; no PVP was detected in the precipitated solids using quantitative NMR (data not shown).

Example 2

Mixtures comprising celecoxib and 1% wt/wt of one of microcrystalline cellulose, gelatin, methyl-D-glucoside and maltodextrin were prepared substantially as described in Example 1. The mixtures were placed in Test I described hereinabove. None of these mixtures were able to maintain a supersaturated celecoxib solution for longer than 4 hours (data not shown).

Example 3

Figure 3:
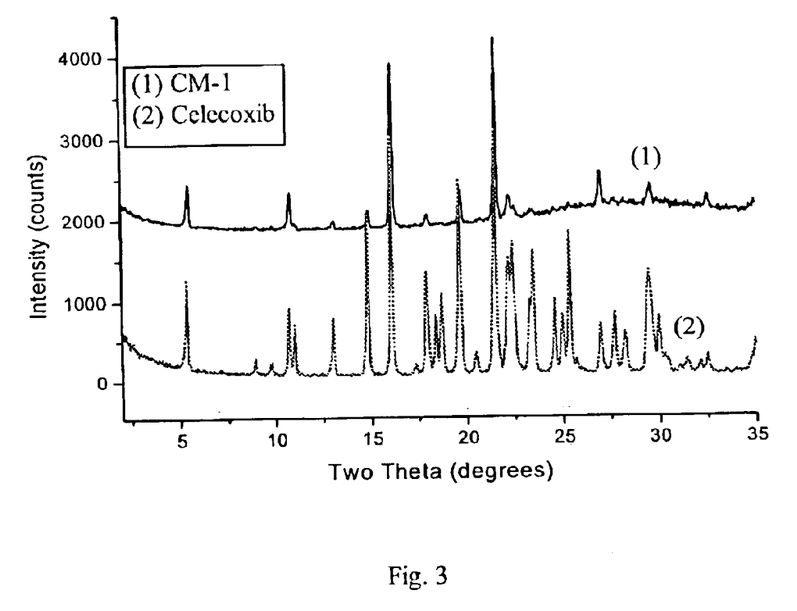
FIG. 3 shows an X-Ray diffraction profile of precipitate separated from comparator mixture CM-1 of Example 3 and of celecoxib in powder form.

A comparator mixture (CM-1) comprising water and celecoxib (500 µg/ml) but no crystallization inhibitor was prepared and was stirred at room temperature for a period of 3 days. After three days of stirring, precipitate was removed from the comparator mixture by filtration; precipitate was analyzed using X-Ray diffraction. FIG. 3 shows the X-Ray diffraction pattern for CM-1 by comparison with that of celecoxib crystalline powder. As seen from these patterns, both materials comprise crystalline material.

Example 4

Seven mixtures, M-7 to M-13, containing celecoxib and HPMC were prepared having compositions shown in Table 2. Mixture M-7 was prepared with grade E4M HPMC while mixture M-5 was prepared with grade E5 HPMC; other mixtures were prepared with various grades of HPMC. The mixtures were prepared by dissolving between 5 and 100 mg of celecoxib per ml of ethanol to form a first solution, dissolving HPMC in water (at 90° C. with stirring) to form a second solution having an HPMC concentration of 0.2% to 2.5% wt/wt, and transferring 1 ml of the first solution into 100 ml of the second solution at a rate of 0.02 ml of first solution per second to form a mixture. Each of the resulting mixtures were stirred at room temperature using a stir bar maintained at 50 rpm for a period of at least 21 days.

TABLE 2

Composition of celecoxib/HPMC mixtures M-7 to M-13

| Composition | M-7 | M-8 | M-9 | M-10 | M-11 | M-12 | M-13 |
|---|---|---|---|---|---|---|---|
| Celecoxib (µg/ml) | 500 | 1000 | 500 | 900 | 500 | 900 | 200 |
| Ethanol (% wt/wt) | 1 | 1 | 1 | 1 | 1 | 1 | 1 |
| HPMC (% wt/wt) | 0.2 | 0.2 | 1 | 1 | 2.5 | 2.5 | 1 |
| Water (% wt/wt) | to 100 | to 100 | to 100 | to 100 | to 100 | to 100 | to 100 |

Figure 4:
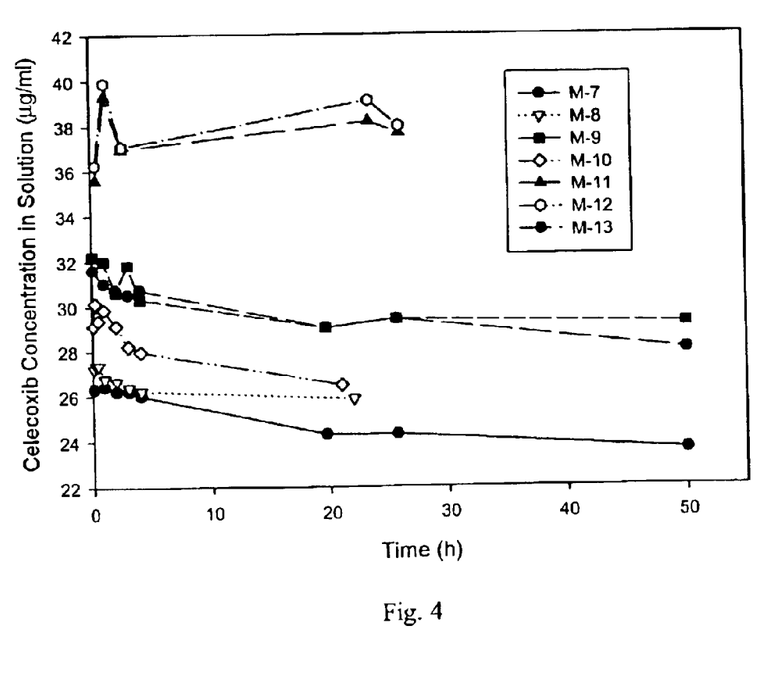
FIG. 4 shows concentration of celecoxib in solution in mixtures M-7 to M-13 of Example 4 at different times after preparation.

At various time points during stirring, aliquots of mixtures M-7 to M-13 were drawn and concentration of celecoxib in solution therein was measured. As shown in FIG. 4, at all drug and HPMC concentrations, celecoxib concentration in solution in the mixtures was greater than 10 µg/ml after 20 hours of stirring. Celecoxib concentration in mixtures M-7, M-9 and M-13 were greater than 10 µg/ml after 50 hours of stirring.

Example 5

Figure 5:
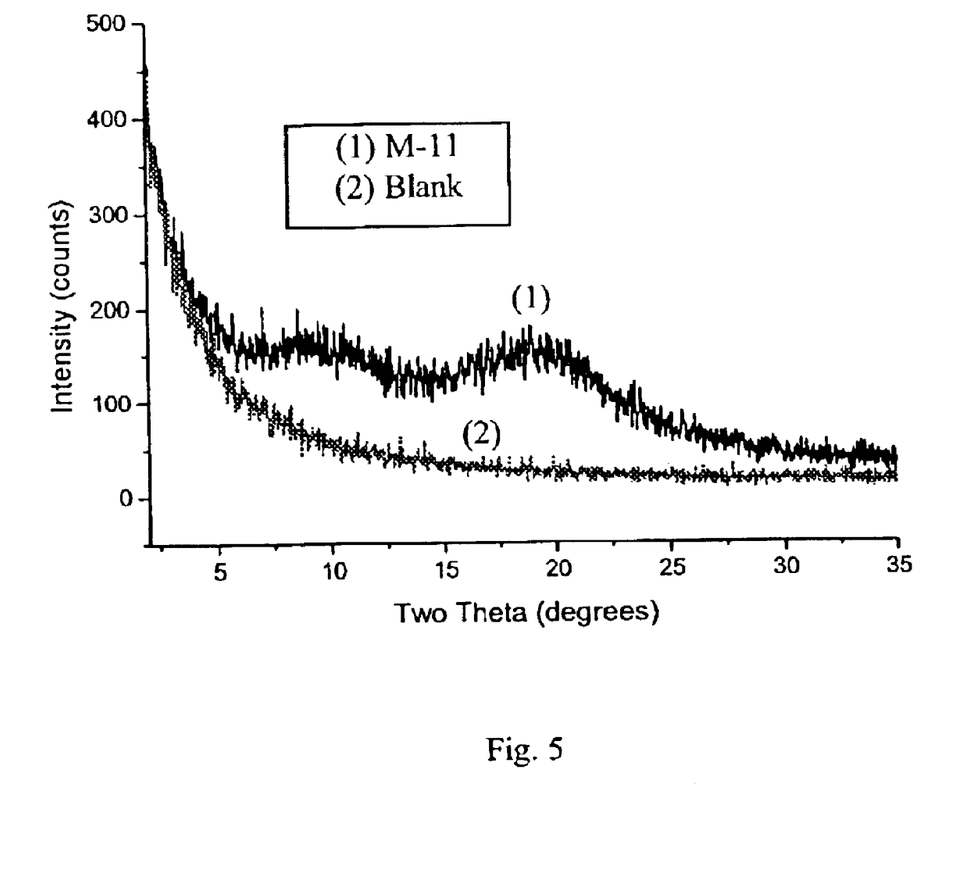
FIG. 5 shows an X-Ray diffraction profile of precipitate separated from mixture M-11 of Example 4 and of a quartz background blank.

A second batch of mixture M-11 of Example 4 was prepared and was stirred (50 rpm) at room temperature for 21 days from date of preparation. After 21 days of stirring, precipitate was removed from the mixture by filtration and was washed with water. The precipitate was then analyzed using X-Ray diffraction (by comparison with a quartz background). As shown in FIG. 5, a signal evidencing non-crystalline material was obtained, and there was no evidence of any crystalline material. These data suggest that celecoxib in precipitate separated from mixture M-11 is amorphous.

Example 6

A second batch of mixture M-7 of Example 4 was prepared and was stirred for a period of seven days. After seven days, precipitate was removed from the mixture by filtration. The precipitate was re-dissolved in a solution comprising 40% deuterium ethanol and 60% deuterium water. Using quantitative NMR, precipitate recovered from mixture M-7 was analyzed and it was determined to contain 38% celecoxib and 62% HPMC, by weight. This procedure was repeated with precipitate removed from a second batch of mixture M-11 of Example 4. Precipitate recovered from mixture M-11 contained 56% celecoxib and 44% HPMC, by weight.

What is claimed is:

1. A process for preparing a celecoxib-crystallization inhibitor composite wherein at least a detectable portion of the celecoxib is in amorphous form, said process comprising the steps of
   (a) dissolving celecoxib in at least one pharmaceutically acceptable solvent for the celecoxib to form a first solution;
   (b) dissolving at least one crystallization inhibitor in at least one pharmaceutically acceptable solvent for the crystallization inhibitor to form a second solution;
   (c) adding the first solution to the second solution at a rate of not more than about 20%, by volume, of the first solution, per second, to form a mixture;
   (d) equilibrating the mixture for a period of time effective to result in precipitation of a celecoxib-crystallization inhibitor composite from the mixture; and
   (e) separating the precipitated celecoxib-crystallization inhibitor composite from the mixture.

2. The process of claim 1 wherein the crystallization inhibitor is a polymer.

3. The process of claim 2 wherein the crystallization inhibitor is HPMC or methylcellulose.

4. The process of claim 1 wherein the celecoxib is present in the first solution at a concentration not less than about 1 mg/ml.

5. The process of claim 1 wherein the celecoxib is present in the first solution at a concentration of about 2.5 to about 400 mg/ml.

6. The process of claim 1 wherein the celecoxib is present in the first solution at a concentration of about 5 to about 200 mg/ml.

7. The process of claim 1 wherein the crystallization inhibitor is present in the second solution in an amount not less than about 0.01%, wt/wt.

8. The process of claim 7 wherein the crystallization inhibitor is present in the second solution in an amount of about 0.1 to about 20%, wt/wt.

9. The process of claim 7 wherein the crystallization inhibitor is present in the second solution in an amount of about 0.1 to about 10%, wt/wt.

10. The process of claim 1 wherein, immediately after formation of the mixture in step (c), the celecoxib is present in dissolved and/or solubilized form in the mixture in an amount of not less than about 25 $\mu$g/ml.

11. The process of claim 10 wherein, immediately after formation of the mixture in step (c), the celecoxib is present in dissolved and/or solubilized form in the mixture in an amount of about 30 $\mu$g/ml to about 5000 $\mu$g/ml.

12. The process of claim 10 wherein, immediately after formation of the mixture in step (c), the celecoxib is present in dissolved and/or solubilized form in the mixture in an amount of about 40 $\mu$g/ml to about 2500 $\mu$g/ml.

13. The process of claim 10 wherein, immediately after formation of the mixture in step (c), the celecoxib is present in dissolved and/or solubilized form in the mixture in an amount of about 50 $\mu$g/ml to about 1000 $\mu$g/ml.

14. The process of claim 1 wherein, immediately after formation of the mixture in step (c), the crystallization inhibitor is present in dissolved and/or solubilized form in the mixture in an amount of not less than about 0.01%, wt/wt.

15. The process of claim 14 wherein, immediately after formation of the mixture in step (c), the crystallization inhibitor is present in dissolved and/or solubilized form in the mixture in an amount of about 0.1 to about 15%, wt/wt.

16. The process of claim 14 wherein, immediately after formation of the mixture in step (c), the crystallization inhibitor is present in dissolved and/or solubilized form in the mixture in an amount of about 0.1 to about 5%, wt/wt.

17. The process of claim 1 wherein, in step (c), the first solution is added to the second solution at a rate of addition of about 0.1% to about 10%, by volume of the first solution, per second.

18. The process of claim 1 wherein, in step (c), the first solution is added to the second solution at a rate of addition of about 0.1% to about 5%, by volume of the first solution, per second.

19. The process of claim 1 wherein said addition step (c) is performed at a temperature of about 18 to about 30° C.

20. The process of claim 1 wherein said addition step (c) is performed at a temperature of about 20 to about 25° C.

21. The process of claim 1 wherein the mixture formed in step (c) is continuously agitated as it is formed.

22. The process of claim 1 wherein said period of time is not less than about 5 minutes.

23. The process of claim 22 wherein said period of time is about 1 to about 60 days.

24. The process of claim 22 wherein said period of time is about 1 to about 30 days.

25. The process of claim 22 wherein said period of time is about 1 to about 21 days.

26. The process of claim 1 wherein said equilibrating step (d) comprises agitating the mixture during said period of time.

27. The process of claim 1 wherein said separating step (e) comprises filtration.

28. A celecoxib-crystallization inhibitor composite prepared according to the process of claim 1.

29. The celecoxib-crystallization inhibitor composite of claim 28 wherein the celecoxib is present therein in an amount of about 10% to about 60%, by weight, and at least a detectable amount of the celecoxib is in amorphous form.

30. The celecoxib-crystallization inhibitor composite of claim 28 wherein the celecoxib is present therein in an amount of about 15% to about 55%, by weight, and at least a detectable amount of the celecoxib is in amorphous form.

31. The celecoxib-crystallization inhibitor composite of claim 28 wherein the celecoxib is present therein in an amount of about 20% to about 50%, by weight, and at least a detectable amount of the celecoxib is in amorphous form.

32. The celecoxib-crystallization inhibitor composite of claim 28 wherein the crystallization inhibitor is present in a total amount of about 10% to about 80%, by weight, and at least a detectable amount of the celecoxib is in amorphous form.

33. The celecoxib-crystallization inhibitor composite of claim 28 wherein the crystallization inhibitor is present in a total amount of about 15% to about 75%, by weight, and at least a detectable amount of the celecoxib is in amorphous form.

34. The celecoxib-crystallization inhibitor composite of claim 28 wherein the crystallization inhibitor is present in a total amount of about 25% to about 65%, by weight, and at least a detectable amount of the celecoxib is in amorphous form.

35. The celecoxib-crystallization inhibitor composite of claim 28 wherein the celecoxib and the crystallization inhibitor are present in a weight ratio of about 1:10 to about 10:1 and at least a detectable amount of the celecoxib is in amorphous form.

36. The celecoxib-crystallization inhibitor composite of claim 28 wherein the celecoxib and the crystallization inhibitor are present in a weight ratio of about 1:5 to about 5:1 and at least a detectable amount of the celecoxib is in amorphous form.

37. The celecoxib-crystallization inhibitor composite of claim 28 wherein the celecoxib and the crystallization inhibitor are present in a weight ratio of about 1:5 to about 2:5 and at least a detectable amount of the celecoxib is in amorphous form.

38. The celecoxib-crystallization inhibitor composite of claim 28 wherein about 10% to 100% of the celecoxib is amorphous celecoxib.

39. The celecoxib-crystallization inhibitor composite of claim 28 wherein about 50% to 100% of the celecoxib is amorphous celecoxib.

40. The celecoxib-crystallization inhibitor composite of claim 28 wherein about 75% to 100% of the celecoxib is amorphous celecoxib.

41. The celecoxib-crystallization inhibitor composite of claim 28 wherein the composite, when maintained in an open dish at room temperature for a period of at least 7 days, exhibits reduced transformation of amorphous celecoxib to crystalline celecoxib by comparison with an otherwise similar celecoxib-crystallization inhibitor composite in which the crystallization inhibitor is replaced by methyl-D-glucoside.

42. A pharmaceutical composition comprising the celecoxib-crystallization inhibitor composite of claim 28 in a total celecoxib dosage amount of about 10 mg to about 1000 mg, and one or more pharmaceutically acceptable excipients.

43. A pharmaceutical composition comprising the celecoxib-crystallization inhibitor composite of claim 28 in a total celecoxib dosage amount of about 25 mg to about 400 mg, and one or more pharmaceutically acceptable excipients.

44. A pharmaceutical composition comprising the celecoxib-crystallization inhibitor composite of claim 28 in a total celecoxib dosage amount of about 50 mg to about 200 mg, and one or more pharmaceutically acceptable excipients.

* * * * *